United States Patent
Hirata et al.

(10) Patent No.: US 7,314,499 B2
(45) Date of Patent: *__Jan. 1, 2008__

(54) METHOD AND DEVICE FOR MANUFACTURING ADVANCED WATER CONTAINING ULTRA-FINE GOLD PARTICLES

(75) Inventors: Yoshihiro Hirata, Kyoto (JP); Yoshio Ueda, Kyoto (JP); Hiroaki Takase, Kyoto (JP); Kazuaki Suzuki, Kyoto (JP)

(73) Assignee: Phild Co., Ltd., Kyoto (JP)

( * ) Notice: Subject to any disclaimer, the term of this patent is extended or adjusted under 35 U.S.C. 154(b) by 734 days.

This patent is subject to a terminal disclaimer.

(21) Appl. No.: 10/468,110

(22) PCT Filed: Feb. 26, 2002

(86) PCT No.: PCT/JP02/01725

§ 371 (c)(1),
(2), (4) Date: Dec. 15, 2003

(87) PCT Pub. No.: WO02/068342

PCT Pub. Date: Sep. 6, 2002

(65) Prior Publication Data

US 2004/0091552 A1    May 13, 2004

(30) Foreign Application Priority Data

Feb. 27, 2001 (JP) ............................. 2001-051341

(51) Int. Cl.
*B22F 9/04* (2006.01)
(52) U.S. Cl. .......................................... 75/361; 75/367
(58) Field of Classification Search .................. 75/360, 75/361
See application file for complete search history.

(56) References Cited

U.S. PATENT DOCUMENTS

| 6,869,626 B1 | 3/2005 | Hirata et al. |
| 6,989,127 B2 | 1/2006 | Hirata et al. |
| 7,108,735 B2 * | 9/2006 | Hirata et al. ................... 75/355 |
| 2004/0107798 A1 | 6/2004 | Hirata et al. |
| 2004/0118244 A1 | 6/2004 | Hirata et al. |
| 2005/0072272 A1 | 4/2005 | Hirata et al. |

FOREIGN PATENT DOCUMENTS

JP        48-84329        11/1973

(Continued)

Primary Examiner—George Wyszomierski
(74) Attorney, Agent, or Firm—Knobbe, Martens, Olson & Bear LLP

(57) ABSTRACT

Produce high-function water useful for consumption as healthy drinking water or in the production of health supplements, cosmetic products, food preservatives, freshness-keeping agents for food, insect repellents or deodorizers, wherein such water contains micro-dispersed ultra-fine gold particles and a small amount of dissolved gold and is produced by constructing in the upper section of a high-pressure water tank a combustion chamber equipped with an injector nozzle for oxygen-hydrogen mixture gas, an ignition device and a gold-rod or gold-wire feeder, igniting the injector nozzle for oxygen-hydrogen mixture gas using the ignition device in the combustion chamber to melt and evaporate the gold rod or wire supplied from the feeder or water in which gold foil was dispersed beforehand and to allow the produced gold vapor to contact high-pressure water, and thereby causing the produced ultra-fine gold particles to float and disperse in water.

2 Claims, 5 Drawing Sheets

FOREIGN PATENT DOCUMENTS

| | | |
|---|---|---|
| JP | 01-231876 | 9/1989 |
| JP | 02-290245 | 11/1990 |
| JP | 04-026701 | 1/1992 |
| JP | 07-330333 | 12/1995 |
| JP | 10-298615 | 11/1998 |

\* cited by examiner

[Figure 1]

Flowchart for producing suspended solution of ultrafine gold particle

ASSAY REPORT

Client Name: Phild Co., Ltd.

Specimen: GOLD WATER

Additional Remarks: ＊＊＊＊

Incorporated Foundation
Japan Food Research Laboratories

| | |
|---|---|
| Tokyo H.Q. | 52-1, Motoyoyogi-machi, Shibuya-ku, Tokyo 151-0062 |
| Osaka Branch | 3-1, Toyotsu-cho, Suita-shi, Osaka 564-0081 |
| Nagoya Branch | 5-13, Ohsu 4-chome, Naka-ku, Nagoya 450-0011 |
| Kyushu Branch | 1-12, Shimogofuku-cho, Hakata-ku, Fukuoka 812-0034 |
| Tama Research Laboratory | 11-10, Nagayama 8-chome, Tama-shi, Tokyo 206-0025 |

The followings are analysis results for the above-identified specimen that was submitted to our laboratory on June 27, 2000.

| Assay Item | Results | Detection Limit | Notes | Analysis Method |
|---|---|---|---|---|
| Gold | 2.9mg/L | | | ICP Luminescence Analysis Method |

The End

ASSAY REPORT

Client Name: Phild Co., Ltd.

Specimen: GOLD AQUAMIRUM

Additional Remarks: ＊＊＊＊

<div style="text-align: right;">

Incorporated Foundation
Japan Food Research Laboratories

</div>

| | |
|---|---|
| Tokyo H.Q. | 52-1, Motoyoyogi-machi, Shibuya-ku, Tokyo 151-0062 |
| Osaka Branch | 3-1, Toyotsu-cho, Suita-shi, Osaka 564-0081 |
| Nagoya Branch | 5-13, Ohsu 4-chome, Naka-ku, Nagoya 450-0011 |
| Kyushu Branch | 1-12, Shimogofuku-cho, Hakata-ku, Fukuoka 812-0034 |
| Tama Research Laboratory | 11-10, Nagayama 8-chome, Tama-shi, Tokyo 206-0025 |

The followings are analysis results for the above-identified specimen that was submitted to our laboratory on June 27, 2000.

| Assay Item | Results | Detection Limit | Notes | Analysis Method |
|---|---|---|---|---|
| Gold | 1.5 mg/L | | | ICP Luminescence Analysis Method |

The End

H:\DOCS\TOS\KOD76Z.002GEN\ASSAY REPORT (2).DOC
072903

ASSAY REPORT

Client Name: Phild Co., Ltd.

Specimen: GOLD WATER

Additional Remarks: ✱✱✱

Incorporated Foundation
Japan Food Research Laboratories

| | |
|---|---|
| Tokyo H.Q. | 52-1, Motoyoyogi-machi, Shibuya-ku, Tokyo 151-0062 |
| Osaka Branch | 3-1, Toyotsu-cho, Suita-shi, Osaka 564-0081 |
| Nagoya Branch | 5-13, Ohsu 4-chome, Naka-ku, Nagoya 450-0011 |
| Kyushu Branch | 1-12, Shimogofuku-cho, Hakata-ku, Fukuoka 812-0034 |
| Tama Research Laboratory | 11-10, Nagayama 8-chome, Tama-shi, Tokyo 206-0025 |

The followings are analysis results for the above-identified specimen that was submitted to our laboratory on February 9, 2001.

| Assay Item | Results | Detection Limit | Notes | Analysis Method |
|---|---|---|---|---|
| Gold | 22mg/L | | | ICP Luminescence Analysis Method |

The End

METHOD AND DEVICE FOR MANUFACTURING ADVANCED WATER CONTAINING ULTRA-FINE GOLD PARTICLES

This application is the U.S. National Phase under 35 U.S.C. §371 of International Application PCT/JP02/01725, filed Feb. 26, 2002, which claims priority of Japanese Patent Application No. 2001-51341, filed Feb. 27, 2001. The International Application was published under PCT Article 21(2) in a language other than English.

FIELD OF THE INVENTION

This invention relates to a method and apparatus for producing high-function water in which ultra-fine gold particles are suspended, and also to high-function water containing ultra-fine gold particles as produced using the method and apparatus.

The invention also relates to various applications of high-function water containing ultra-fine gold particles.

BACKGROUND OF THE INVENTION

Since ancient times, gold had been held in a high position as the most valuable precious metal and used mainly in the manufacture of ornaments and other objects that were considered treasures. In recent years, a recognition of the health-promoting benefits of gold prompted production of healthy bracelets made of pure gold, sake wines containing gold foils, and so on. However, these "health" products failed to prove sufficient efficacies on human health beyond their luxury image derived from the use of expensive 24K gold. These days, the healthful benefits of gold are again drawing the attention of today's health-conscious consumers, and it is now known that gold exhibits its health-promoting functions more prominently in the forms of gold ions and fine gold particles than in solid or foil form.

There are keen interests in the potential health-promoting functions and healing effects of gold ions and fine gold particles. Gold is now known to have significant health benefits ("*Gold Water" Cured Intractable Diseases the Doctors Gave Up Treating*, written by Tonpu Takada), and the public is awaiting further technological advance in this field. In the use of gold ions and fine gold particles in a water solution or aqueous dispersion, however, several issues must be addressed before these applications can be put to practical use.

As described above, waters containing gold in some form are widely known (see p. 64 of the aforementioned book). However, a majority of these products have either gold foil or gold powder simply dispersed in water. Since the methods to melt gold itself have been limited to those using aqua regia or a gold electrolyte, it has been extremely difficult to dissolve gold ions or fine gold particles in water.

Efforts have been underway to develop new technologies that will solve these problems and embody the potential health-promoting functions and healing effects of gold ions and fine gold particles. However, only a limited number of technologies relating to this field are disclosed in the Publication of Unexamined Patent Application, which is considered a yardstick for the progress of technological development. This suggests that the need for new technology regarding the application of gold ions and fine gold particles is still very high.

The published technologies include: the technology to mix with polyolefin molding resin an inorganic antibacterial agent formulated by fixing gold ions or other ions that have an antibacterial property to a zeolite ion-exchange group, in order to provide an antibacterial beverage tank that is resistant to saprophytic bacteria eluting from the tank material such as polyethylene and thereby prevents the negative effects of dissolved chemicals to preserve the taste and flavor of the drink (Registered Japanese Utility Model No. 3046284); the technology to retain mineral carriers in water and stimulate them by adding acid or conducting electrolysis to release minerals into water, in order to provide mineral water containing gold ions and other minerals beneficial to the human body (Japanese Patent Application Laid-open No. 9-220580); the technology to dissolve gold or other heavy metal into an acid ion water of pH 2.6 to 4.5 or oxidation potential water of pH 2.7 or below, both of which are produced in an electrolytic water purifier, in order to produce low-cost antiseptic water offering excellent sterilizing effect (Japanese Patent Application Laid-open No. 9-10772); and the technology to uniformly mix gold foil or other additive with crushed ice granules, pack an ice-making container with the mixture of additive and ice granules, and then gradually introduce water from the bottom of the container to form ice, in order to produce blocks of healthy ice in which gold foil or other additive is distributed evenly (Japanese Patent Application Laid-open No. 5-280841).

However, except for the technology to retain mineral carriers in water and stimulate them by adding acid or conducting electrolysis to release minerals into water, in order to provide mineral water containing gold ions and other minerals beneficial to the human body (Japanese Patent Application Laid-open No. 9-220580), which is generating an interest, these published technologies are far from solving the aforementioned problems, and essentially they are not capable of providing solutions.

However, except for the technology to retain mineral carriers in water and stimulate them by adding acid or conducting electrolysis to release minerals into water, in order to provide mineral water containing gold ions and other minerals beneficial to the human body (Japanese Patent Application Laid-open No. 9-10772), which is generating an interest, these published technologies are far from solving the aforementioned problems, and essentially they are not capable of providing solutions.

Application of the activity of gold ions and ultra-fine gold particles to the production of bioactive materials, health foods, medicines, etc., provides an important area where technological advance must be sought, since the results will directly affect our daily life. As use of gold ions and ultra-fine gold particles is expected to grow, the public eagerly awaits further development of application technologies.

SUMMARY OF THE INVENTION

As explained above, gold ions and ultra-fine gold particles have a high potential in terms of embodying health-promoting functions and healing effects, and there are demands for further technological advance in this field. The basic form of application is considered a water solution or aqueous dispersion containing gold ions or ultra-fine gold particles. However, several issues must be addressed before these solutions and dispersions can be put to practical use. For example, it is difficult to dissolve gold ions and fine gold particles in water. Traditionally the producers have simply mixed gold foil or gold powder into water or achieved dissolution using a gold electrolyte. However, such methods require high production costs and are therefore not economically viable, and the obtained products did not exhibit sufficient health-promoting functions. Potentially damaging effects of chemical electrolyte on human health have not been verified, either. These are among the technical problems that need to be resolved.

While there are significant demands for technological development in the application of gold ions and ultra-fine gold particles to bioactive materials, health foods, medicines, etc., the specific technologies available today have not reached a satisfactory level.

Therefore, the inventors have carried out extensive studies in order to identify ways of producing high-function water containing ultra-fine gold particles and offering high bioactivity, under the assumption that providing drinkable water containing gold ions or ultra-fine gold particles will allow consumers to improve their health and heal various conditions in a very simple manner by utilizing the health-promoting functions of gold ions and ultra-fine gold particles. As a result, the inventors have found that water containing gold ions or ultra-fine gold particles produced using the method and apparatus explained later has significant benefits on our health, and thereby developed the present invention.

In other words, the present invention provides a method for producing high-function water containing ultra-fine gold particles, being characterized by a construction in the upper section of a high-pressure water tank of a combustion chamber equipped with an injector nozzle for oxygen-hydrogen mixture gas and an ignition device, wherein the injector nozzle for oxygen-hydrogen mixture gas is ignited by the ignition device to melt and evaporate the material gold and allow the produced gold vapor to contact high-pressure water, and thereby causing the produced ultra-fine gold particles to float and suspend in water.

The high-function water containing ultra-fine gold particles as obtained in this method is a ultra-micro-dispersion of ultra-fine gold particles in water where a small amount of gold is also dissolved in water, as shown in the analysis certificates provided in FIGS. 3 and 4.

The present invention also provides an apparatus for producing high-function water containing ultra-fine gold particles, being characterized by its construction-a high-pressure water tank which is a pressure-resistant container having a combustion chamber inside that is equipped with an injector nozzle for oxygen-hydrogen mixture gas, an ignition device, and a gold-rod or gold-wire feeder.

Furthermore, the present invention provides an apparatus for producing high-function water containing ultra-fine gold particles, wherein the apparatus is equipped with a water electrolyzer for production of oxygen-hydrogen mixture gas as an adjunct facility, in addition to the components describe above. The invention aims to utilize the high-function water containing ultra-fine gold particles obtained through the aforementioned method or apparatus.

The high-function water obtained by the present invention offers very high utility in the production of healthy drinking waters, cosmetic products, food preservatives, freshness-keeping agents for food, insect repellents, deodorizers, etc.

Material gold used in the method and apparatus provided by the present invention may be fed in rod or wire form sequentially from a gold-rod or gold-wire feeder being equipped inside the high-pressure water tank, or gold foil may be dispersed in the water stored in the high-pressure water tank.

While the present invention can use gold rod or wire or gold foil as material, use of gold rod or wire being fed from the aforementioned gold feeder yields a higher productivity of high-function water compared with when gold foil is dispersed in water beforehand. One reason for a lower productivity associated with the pre-dispersion of gold foil in water is that the flame from the injector nozzle for oxygen-hydrogen mixture gas cannot act upon the gold foil suspended in high-pressure water and therefore sufficient thermal energy cannot be transferred to the gold foil.

BRIEF DESCRIPTION OF THE DRAWINGS

FIG. 3: Analysis result of water obtained from gold foil and distilled water FIG. 4: Analysis result of water obtained from gold foil and tap water FIG. 5: Analysis result of water obtained from gold rod and distilled water

DESCRIPTION OF THE SYMBOLS

Figure 1:
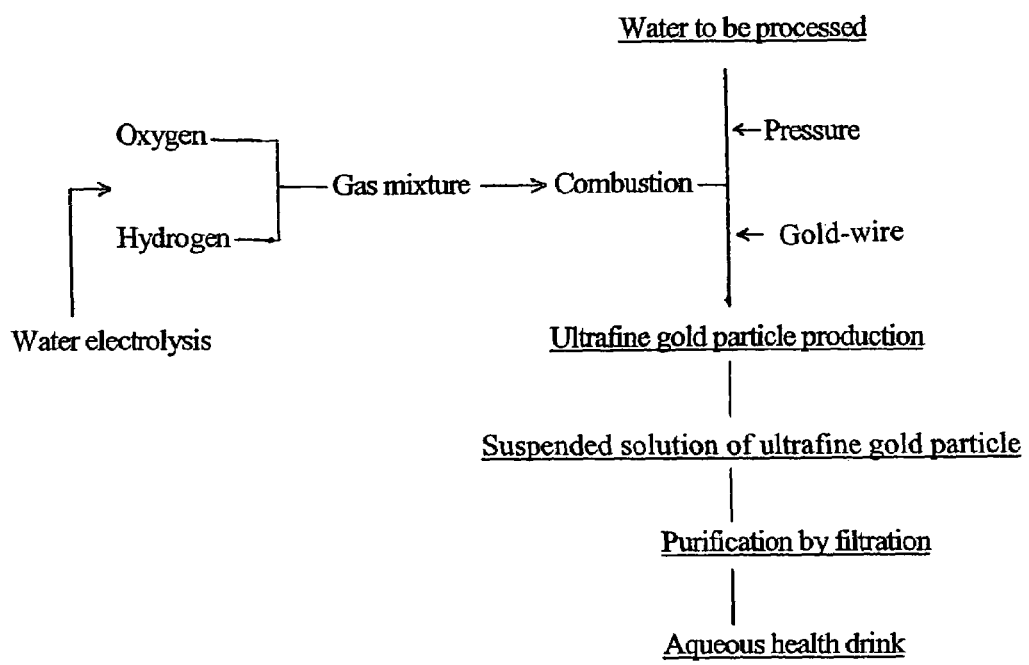
FIG. 1: Flow chart illustrating a process overview of the present invention

1: Production apparatus for suspension of ultra-fine gold particles in water
2: High-pressure tank
3: Pressurized water
4: Suspended ultra-fine gold particles
5: Injector nozzle
6: Combustion gas
7: Combustion chamber
8: Water inlet
9: Hydrogen supply channel
10: Oxygen supply channel
11: Agitator
12: Ignition device
13: Pump
14: Filter device
15: Product
16: Water electrolyzer
17: Electrolytic container
18: Water
19: Electrode plate
20: Power supply
21: Gold rod or wire
22: Feeder

BEST MODE FOR CARRYING OUT THE INVENTION

The present invention is characterized by the production of a dispersion of ultra-fine gold particles of sub-micron order in water that are smaller than normal fine gold particles, and the utilization of the dispersion water thus produced. The obtained water offers notably higher functions including health-promotion functions, and its physical properties ensure safety for human consumption just like normal water.

The high-function water obtained by the present invention can be consumed directly as healthy drinking water or may be used as the main ingredient or secondary ingredient in the production of health supplements, cosmetic products, food preservatives, freshness-keeping agents for food, insect repellents, deodorizers, etc.

The construction of the present invention is explained using the drawings.

The present invention provides a method for producing high-function water containing ultra-fine gold particles, wherein the water is produced by a high-pressure water tank having a combustion chamber inside that is equipped with an injector nozzle for oxygen-hydrogen mixture gas, an ignition device, and a gold-rod or gold-wire feeder. The injector nozzle for oxygen-hydrogen mixture gas is ignited by the ignition device in the combustion chamber to melt and evaporate the gold rod or wire fed from the gold-rod or gold-wire feeder and allow the produced gold vapor or droplets to contact high-pressure water, thereby causing the produced ultra-fine gold particles to float and suspend in water. FIG. 1 gives an overview of this process.

Figure 2:
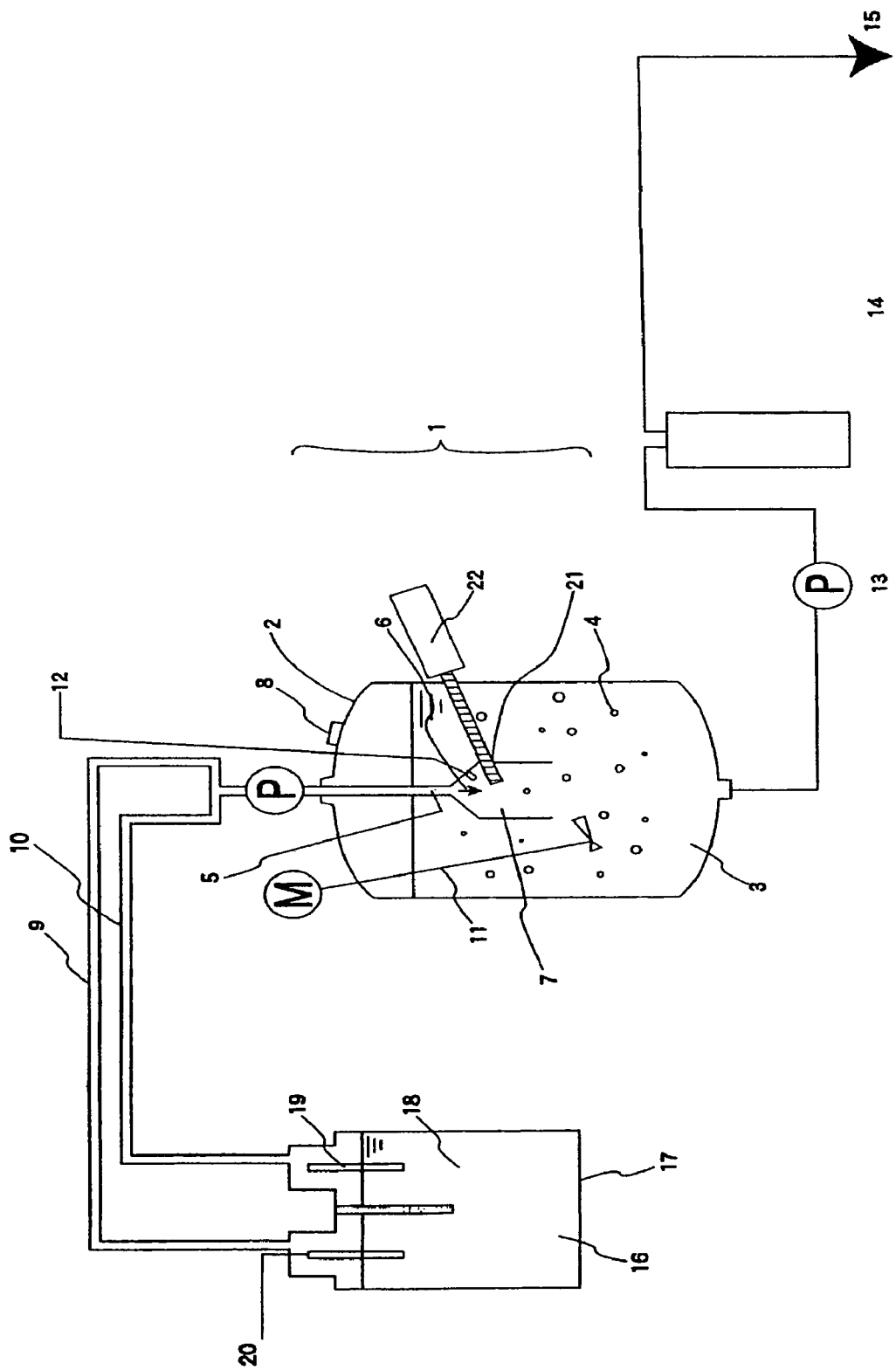
FIG. 2: Schematic drawing of an apparatus for producing water containing ultra-fine gold particles as provided by the present invention

The present invention also involves the development of an apparatus that embodies the aforementioned method for producing high-function water containing ultra-fine gold particles. FIG. 2 illustrates this production apparatus.

The basic production method provided by the present invention is to introduce water into a pressure tank and pressurize it to a high pressure level, inject a hydrogen-oxygen mixture gas from the injector nozzle into the combustion chamber provided inside the pressure tank to completely burn the mixture gas, and then instantly melt and evaporate the supplied gold rod or wire fed in the fully burned vapor gas of ultrahigh temperature obtained above, thereby allowing the produced gold vapor or droplets to contact and suspend in high-pressure water. Through this process extremely fine gold particles of micron scale are produced and micro-dispersed in water. Use of a hydrogen-oxygen mixture gas yields the most efficient and stable combustion inside the combustion chamber, and high pressure is needed to ensure stable combustion.

The present invention also allows use of a gold dispersion in which gold foil is dispersed beforehand, instead of feeding material gold in rod or wire form as explained above.

An oxygen-hydrogen mixture gas (mixed at a ratio of 1:2) used in the aforementioned production method or apparatus produces a high-temperature combustion gas. It is considered that gold rod or wire (melting point: 1064° C., boiling point: 2800° C.) instantly melts and evaporates in this combustion gas and enters water to become ultra-fine gold particles.

The produced suspension of ultra-fine gold particles in water may be used directly without filtering. Depending on the application, this water can also be filtered using a filter material, etc., to remove a trace amount of fine gold particles that are larger than ultra-fine particles of micron scale, in order to provide water in which only ultra-fine gold particles are suspended. In addition, the water also contains a small amount of gold in a dissolved state, as explained above and evidenced in the analysis results in FIGS. 3 and 4.

Small pieces of gold and fine gold particles that are trapped by the filter can be recovered via backwash and reused as material, as appropriate, for improved economy.

In the production method provided by the present invention, the amounts of hydrogen and oxygen gases must be strictly controlled to maintain a ratio of two to one. The reaction time and the amount of fuel (mixture gas) to be burned must also be controlled. An insufficient reaction time does not produce a dispersion having the expected health benefits, while an excessive reaction time reduces the tastiness of the water.

The apparatus for producing healthy water containing ultra-fine gold particles shown in FIG. 2 is an apparatus (1) that produces a suspension of ultra-fine gold particles in water and consists of a high-pressure tank (2), an injector nozzle (5) for oxygen-hydrogen mixture gas (6) and a combustion chamber (7). As adjunct facilities, a water electrolyzer (16) to supply the material hydrogen-oxygen mixture gas and a filter device (14) to filter the obtained dispersion are installed.

The production container used in the present invention is a pressure-resistant tank (high-pressure tank, 2) made of metal, or preferably steel, into which pressurized water (3) is supplied from an inlet (8). The container is also equipped with a feeder (22) for supplying material gold rod or wire (21), which introduces a specified amount of gold into the flame at the nozzle. The combustion chamber (7) is provided near the injection nozzle (5) for the hydrogen-oxygen mixture gas (6) supplied through a hydrogen supply channel (9) and oxygen supply channel (10), and the mixture gas is ignited with an ignition device (12) and burned completely. The material gold instantly melts and evaporates in this fully burned vapor gas of ultrahigh temperature, and then enters water, thereby producing a dispersion of ultra-fine gold particles.

The production container used in the present invention is a pressure-resistant tank (high-pressure tank, 2) made of metal, or preferably steel, into which pressurized water (3) is supplied from an inlet (8). The container is also equipped with a feeder (22) for supplying material gold rod or wire (21), which introduces a specified amount of gold into the flame (6) at the nozzle. The combustion chamber (6) is provided near the injection nozzle (5) for the hydrogen-oxygen mixture gas (6) supplied through a hydrogen supply channel (9) and oxygen supply channel (10), and the mixture gas is ignited with an ignition device (12) and burned completely. The material gold instantly melts and evaporates in this fully burned vapor gas of ultrahigh temperature, and then enters water, thereby producing a dispersion of ultra-fine gold particles.

The obtained water, which contains dispersed ultra-fine gold particles and a small amount of dissolved gold, may be used directly, or channeled through a filter housing (filter device, 14) with a pump (13) to be output as product (15). As for the type of filter, hollow-fiber membrane of micron order is preferred to ion-exchange membrane or reverse-osmosis membrane, since hollow-fiber membrane can effectively let pass only ultra-fine particles.

As for the production scale contemplated by the present invention, to produce one ton of dispersion the apparatus should be operated for around two hours at a mixture-gas injection rate of approximately 5 liters per second. Applying too high a gas pressure may damage the apparatus structure, while an insufficient gas pressure cannot achieve sufficient heat generation and therefore the heated material gold will not become fragmented to sufficiently small pieces. In such a case, water containing ultra-fine gold particles cannot be produced efficiently, since large pieces of gold drop directly into water. A preferred mixture-gas pressure is approximately 3.5 atmospheres. Water should be compressed to approximately 2 atmospheres in the pressure tank.

In the apparatus provided by the present invention, material-gas cylinders may be used instead of a water electrolyzer (16) to supply the fuel, i.e., oxygen and hydrogen. However, hydrogen and oxygen produced via water electrolysis are pure, so use of a water electrolyzer should facilitate the supply of material hydrogen and oxygen.

The water electrolyzer (16) may be a commercial unit consisting of a container (17) in which water (18) and electrode plates (19) are placed. The electrodes are connected to a power supply (20).

Acid or alkali material water is hydrolyzed to generate oxygen gas at the anode and hydrogen gas at the cathode. These gases are then fed as material gases for combustion.

In this apparatus, installation of a filter housing (14) is recommended if dispersed ultra-fine gold particles or undispersed ultra-fine gold particles in water must be removed. Depending on the application, the water produced by this apparatus may be filtered using a filter material, etc., to remove fine gold particles larger than ultra-fine particles, so that water in which only ultra-fine particles are suspended can be obtained. The fine gold particles trapped by the filter may be recovered and reused as material for improved economy.

The water containing a small amount of dissolved gold and dispersed ultra-fine gold particles, as produced by the aforementioned method and apparatus, may be consumed directly.

The recovered water can be refined simply by installing a filter housing (14) in which hollow-fiber membranes of micron order are set and by filtering/removing fine gold particles not required in the intended high-function water. As an example of filter application using a hollow-fiber membrane filter, hollow-fiber membranes of 50 microns, 25 microns, 3 microns, 0.5 micron and 0.1 micron can be set in this order at a position where the produced water is released from the reaction tank, in order to sequentially filter the water. This way, drinking water meeting the food sanitation standards will be obtained.

The high-function water obtained by the present invention may be used as healthy drinking water or an ingredient of health supplements, cosmetic products, food preservatives, freshness-keeping agents for food, insect repellents, deodorizers, etc., as explained earlier.

Samples of high-function water obtained by the present invention were sent to a third-party laboratory (Japan Food Research Laboratories) for analysis (IPC emission spectrochemical analysis). The results (Au contents) are shown in the figures.

FIG. 3 shows the analysis result in Au content of water produced by dispersing gold foil in pressurized, distilled water, while FIG. 4 shows the analysis result of water produced in the same manner except that tap water (in Kyoto City) was used instead of distilled water.

FIG. 5 shows the analysis result of water produced by burning gold rod in pressurized, distilled water.

The respective analysis results are as follows:

| | |
|---|---|
| Au content when distilled water is used (material: gold foil) | 2.9 mg/L |
| Au content when tap water is used (material: gold foil) | 1.5 mg/L |
| Au content when distilled water is used (material: gold rod) | 22.0 mg/L |

It is assumed with confidence that the high-function water in which gold is dissolved and ultra-fine gold particles are micro-dispersed will make groundbreaking drinking water that can answer the needs of today's health-conscious consumers. Although the mechanism of healthful benefits and specific details of bioactivation effects expected of the suspension of ultra-fine gold particles in water are still unknown at the present, the test subjects who were given a sample of this water reported a notable improvement in their physical condition and marked reduction of fatigue, as explained later. These results confirm the actual efficacy of the water. It is considered that the ion-emission effect of ultra-fine gold particles, very large active area of the ultra-fine particles, unique characteristics of gold as a precious metal, and chemical/physical stability of gold, are all combined to produce bioactivation effects in our body such as improved stabilization and promotion of intestinal absorption.

An embodiment of the present invention is explained in the following example using the drawings. However, the invention is not limited to the example provided.

EXAMPLE

The apparatus (1) shown in FIG. 2 consists of a high-pressure tank (2), an injector nozzle (5) for hydrogen-oxygen mixture gas (6) and a mixture-gas combustion chamber (7), and represents an overall embodiment of the method for producing a suspension of ultra-fine gold particles in water.

As adjunct facilities, a water electrolyzer (16) to supply fuel, i.e., hydrogen-oxygen mixture gas and a filter device (15) to refine the obtained suspension water are installed.

The specific operation of the present invention is explained below. The production container should be a pressure-resistant tank (high-pressure tank, 2) made of metal, or preferably steel, into which pressurized water (3) is supplied from an inlet (8). Material gold (21) is supplied in rod or wire form from a feeder (22). A combustion chamber (7) is provided near the injection nozzle (5) for the hydrogen-oxygen mixture gas (6) supplied through a hydrogen supply channel (9) and oxygen supply channel (10), and the mixture gas is ignited with an ignition device (12) and burned completely. The material gold instantly melts and evaporates in this fully burned vapor gas of ultrahigh temperature, and then enters the pressurized water (3), thereby producing a suspension of ultra-fine gold particles (4) in water. This ultra-fine gold particle dispersion is then channeled through a filter housing (14) via a pump (13), if necessary, and then output as product (15).

If gold foil is used as the material, the aforementioned gold-rod or gold-wire feeder (22) may be omitted.

The operating conditions are summarized below:

| | |
|---|---|
| Pressurized water: 1 ton | Pressure: 2 kg/cm$^2$ |
| Oxygen-hydrogen mixture gas (mixed at a ratio of 1:2): 5 L/sec, 3.5 atmospheres | |
| Injection time: 2 hours | |
| Feed amount of gold wire: 50 g | |
| Produced suspension water: Approx. 1 ton | |

The produced suspension water was filtered through hollow-fiber membranes of 50 microns, 25 microns, 3 microns, 0.5 micron and 0.1 micron set in this order, in order to obtain high-function water in which ultra-fine gold particles are suspended.

Field Test of High-Function Water

A total of 10 adult subjects comprising males and females were asked to drink high-function water in which ultra-fine gold particles are suspended, in order to verify the efficacies and benefits of the water in promoting health and healing diseases. Details are given below.

Amounts and Conditions of Water

| | | |
|---|---|---|
| Amount consumed per day: | Around 1 glass | 5 persons |
| | Up to 3 glasses | 2 persons |
| | 4 glasses or more | 3 persons |

| | -continued | |
|---|---|---|
| Taste: | Tasty | 9 persons |
| | Tasteless | 1 person |
| Smell: | Not noticeable | 9 persons |
| | Noticeable | 1 person |

Efficacy Verification Standards

| | |
|---|---|
| Effective on 5 out of 10 persons: | ⊙ |
| Effective on 3 out of 10 persons: | ○ |
| Effective on 1 out of 10 persons: | Δ |
| Not effective on anyone: | X |
| Comparison water: | A mixture of water with gold foil and fine gold particles with an average particle size of 1 mm (10 mg of gold per 10 cc of water) produced via prior art = The comparison water was given to a different sample comprising 10 adults. |

Table 1 shows the field test results of the water produced by the present invention and the comparison water.

TABLE 1

| Item | Water produced by the present invention | Comparison water |
|---|---|---|
| Improvement of physical condition | ⊙ | Δ |
| Reduction of fatigue | ⊙ | Δ |
| Increase in appetite | ○ | X |
| Normalization of digestive function | ⊙ | Δ |
| Lowering of blood pressure | ⊙ | X |
| Healing of gastric inflammation | ○ | X |
| Reduction of eye fatigue | ○ | X |

A majority of subjects found the water produced by the present invention easy to drink in terms of taste and smell.

The results shown in Table 1 also reveal the remarkable effects of the water in improving physical condition, increasing appetite and promoting general health.

Industrial Field of Application

As explained above, the present invention provides a new method and apparatus for producing a dispersion of ultra-fine gold particles, as well as high-function water utilizing the newly obtained suspension of ultra-fine gold particles in water. It allows for the production of a suspension of ultra-fine gold particles in water in a simple, inexpensive manner. If the obtained dispersion of ultra-fine gold particles is used as drinking water, such drinking water should offer remarkable health-promoting functions, such as improvement of physical condition and increase in appetite, by utilizing the bioactivation effects of ultra-fine gold particles.

What is claimed is:

1. A method for producing high-function water containing ultra-fine gold particles, which comprises:

preparing a combustion chamber equipped with an injector nozzle for oxygen-hydrogen mixture gas, an ignition device and a gold-rod or gold-wire feeder inside a high-pressure water tank;

igniting said injector nozzle for oxygen-hydrogen mixture gas by the ignition device in said combustion chamber;

melting and evaporating gold as a material and allowing the resultant gold vapor to contact high-pressure water; and causing the resultant ultra-fine gold particles to float and disperse in water.

2. The method for producing high-function water containing ultra-fine gold particles as described in claim 1, wherein said gold as a material is gold rod, wire or foil.

* * * * *